United States Patent
Lopes

(10) Patent No.: US 6,169,494 B1
(45) Date of Patent: Jan. 2, 2001

(54) BIOTELEMETRY LOCATOR

(75) Inventor: Robert Joseph Lopes, Branchburg Township, Somerset County, NJ (US)

(73) Assignee: Lucent Technologies, Inc., Murray Hill, NJ (US)

( * ) Notice: Under 35 U.S.C. 154(b), the term of this patent shall be extended for 0 days.

(21) Appl. No.: 09/026,974

(22) Filed: Feb. 20, 1998

(51) Int. Cl.[7] .............................. G07D 7/00; H04Q 5/22; G08C 19/12

(52) U.S. Cl. .................... 340/825.49; 340/5.8; 340/5.82; 340/870.17; 340/870.28; 340/5.83

(58) Field of Search .................. 340/825.49, 825.54, 340/825.34, 825.44, 825.31, 870.17, 870.16, 870.28, 573.1, 573.4, 825.36, 5.8, 5.82, 5.83; 342/42, 450

(56) References Cited

U.S. PATENT DOCUMENTS

| | | |
|---|---|---|
| 4,510,495 | 4/1985 | Sigrimis et al. . |
| 4,593,284 | 6/1986 | Clifford et al. . |
| 4,598,272 * | 7/1986 | Cox ...................................... 340/539 |
| 4,686,498 | 8/1987 | Carr et al. . |
| 4,689,621 | 8/1987 | Kleinberg . |
| 4,696,054 | 9/1987 | Tsugei et al. . |
| 5,139,021 * | 8/1992 | Sekii et al. ............................. 128/630 |
| 5,153,584 * | 10/1992 | Engira .............................. 340/870.18 |
| 5,218,344 * | 6/1993 | Ricketts ................................. 340/573 |
| 5,241,961 | 9/1993 | Henry . |
| 5,307,817 | 5/1994 | Guggenbuhl et al. . |
| 5,395,366 | 3/1995 | D'Andrea et al. . |
| 5,415,181 | 5/1995 | Hogrefe et al. . |
| 5,419,336 | 5/1995 | Margison . |
| 5,532,709 | 7/1996 | Talty . |
| 5,589,840 | 12/1996 | Fujisawa . |
| 5,652,570 * | 7/1997 | Lepkofker ............................. 340/573 |
| 5,682,605 | 10/1997 | Salter . |
| 5,748,103 * | 5/1998 | Flach et al. ...................... 340/870.07 |
| 5,917,414 * | 6/1999 | Oppelt et al. ...................... 340/573.1 |

* cited by examiner

Primary Examiner—Michael Horabik
Assistant Examiner—M. Phan
(74) Attorney, Agent, or Firm—William H. Bollman

(57) ABSTRACT

A biotelemetry tracking and locating system uses a person's own physical or biological measurement as an identification code used by a tracked unit, e.g., a bracelet worn by a child, to track and/or locate the person from a tracking/locating unit, e.g., worn or carried by a parent. The tracking/locating unit includes a transmitter and optionally a receiver. The tracking/locating unit detects a combination of encoded biological measurements (e.g. body temperature, and/or heart rate) and combines the biological measurements into a substantially unique ID code. The tracking/locating unit may be carried, e.g., by a parent to track the continued presence within a reception range of, e.g., a child wearing the tracked unit. A directional antenna, e.g., a YAGI type antenna, in the tracking/locating unit allows the tracking/locating unit to determine which direction the tracked unit is in, e.g., with respect to the tracking/locating unit. A panic button can be included with the tracked unit to allow a child or other person wearing a tracked unit to alert the tracking person, e.g., a parent to a dangerous situation. The tracking unit may include a paging button to output a paging signal to desired tracked units, which is emitted visually or aurally at the tracked unit.

20 Claims, 4 Drawing Sheets

BIOTELEMETRY LOCATOR

BACKGROUND OF THE INVENTION

1. Field of the Invention

The present invention relates generally to a remote tracking and/or locating system, and more specifically to an improved remote locating system that utilizes a person's biological measurements as an identification code.

2. Background of Related Art

FIG. 4 shows a prior art device to aid in the retrieval of lost children or people. The bracelet assembly 90 includes an elongated flexible band 91. There is a transparent portion 92 through which one can read identification information 93. The identification information 93 can include a person's name, phone number, address, etc. This information is used by others to help the lost person find their way home, or to contact a parent or guardian. The bracelet 90 is most commonly made of a plastic type material which is looped around the wearer's wrist and fastened. An attaching means 94 is used to snug the bracelet 90 around the user's wrist. The identification information 93 is usually written, typewritten or imprinted on a piece of paper or similar receiving medium and is affixed to the bracelet or slipped under the transparent portion 92.

One disadvantage with conventional bracelets is that the identification information is generally printed with ink which can be rubbed, smudged or possibly washed off. The plastic band 91 can be easily torn or cut off. Also, no verification that the proper person is wearing the bracelet is difficult at best by people who are not familiar with the wearer or identified person. Moreover, beyond visual verification, there is no way to detect the location or presence of the bracelet 90.

There is a need for a portable tracking and/or locating system which will uniquely identify the presence and location of an individual.

SUMMARY OF THE INVENTION

In accordance with the principles of the present invention, a biotelemetry locating system used to track a desired individual is provided. In one aspect, a biotelemetry locating system comprises a tracked unit comprising an antenna, a microprocessor, a battery, and at least one biological sensor. A tracking/locating unit is also provided comprising an antenna, and a microprocessor. The tracked unit is capable of transmitting an identifying code based on data from the biological sensor, to the tracking/locating unit.

In another aspect, a tracked unit comprises a processor, and a biotelemetry sensor in communication with the processor to measure a biological parameter of a wearer of the tracked unit. A code generator generates a substantially unique ID code corresponding to the wearer of the tracked unit, and a transmitter transmits the substantially unique ID code.

In yet another aspect of the present invention, a tracking/locating unit is provided, comprising an antenna, a processor, a receiver circuit in communication with the processor, and a display to display a location of a tracked unit based on a reception by the receiver of a signal including a biological parameter of a wearer of the tracked unit.

The foregoing has outlined rather broadly the more pertinent and important features of the present invention in order that the detailed description of the invention that follows may be better understood so that the present contribution to the art can be more fully appreciated. It should be appreciated by those skilled in the art that the conception and the specific embodiments disclosed may be readily utilized as a basis for modifying or designing other structures and method for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The present invention will be more fully understood by reference to the following detailed description thereof when read in conjunction with the attached drawings, and wherein.

DETAILED DESCRIPTION OF ILLUSTRATIVE EMBODIMENTS

The present invention provides a tracked unit which transmits a unique identifying signal based on at least one biological parameter of the wearer, e.g., specific body temperature, pulse rate, and/or a scanned image of, e.g., a fingerprint, to generate a relatively unique code for identifying and/or locating a specific wearer.

The biotelemetry system of the present invention is used to allow a person, e.g., a parent or guardian to track a person under their care, e.g., a child.

Figure 1:
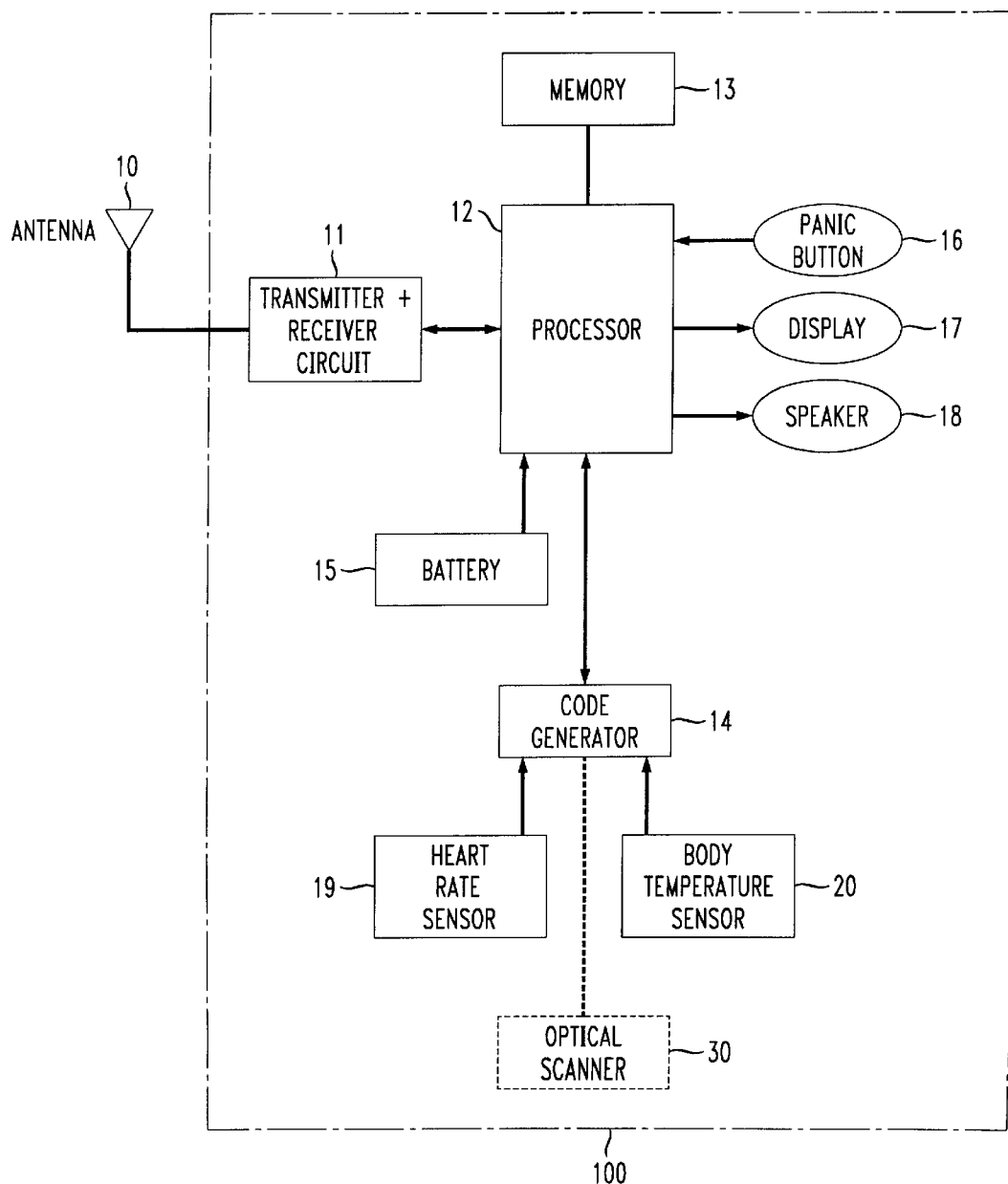
FIG. 1 is a block diagram of a tracked unit according to one embodiment of the present invention.
Figure 2:
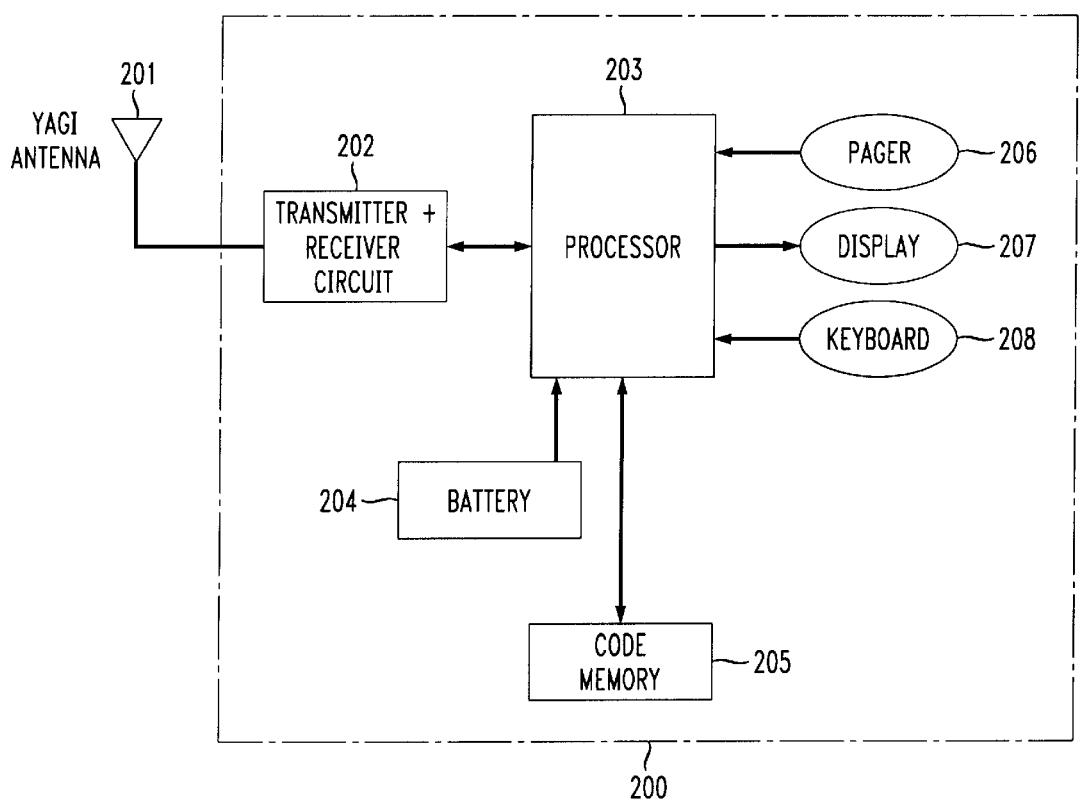
FIG. 2 shows a block diagram of a tracking/locating unit for tracking the tracked unit of FIG. 1, in accordance with the principles of the present invention.

The tracked unit 100 as shown in FIG. 1 is used in conjunction with a tracking/locating unit 200 as shown in FIG. 2. When an individual first puts the tracked unit 100 on, at least one biological parameter is measured to form the basis of a substantially unique identifying code corresponding to the wearer of that tracked unit 100. A parent having a tracking/locating unit 200 presses a paging key to select a specific child or all children, and a signal is sent from the parent's tracking/locating unit 200 to the tracked units 100 worn by the children.

Receivers with directional antennas are well known. For instance, a highly directional YAGI dipole antenna was originally described in the article entitled ABeam Transmission of Ultra Short Waves@ by H. Yagi in Proceedings of the IRE, vol. 16, June 1928, pp. 715–741. YAGI antennas produce substantial directivity by use of parasitic director and reflector dipoles coplanar with the driven dipole. Moreover, physical configurations of conventional YAGI dipole array antennas are known and discussed, for example, in the article by C. A. Chen and D. K. Cheng entitled AOptimum Element Lengths for Yagi-Uda Arrays@ published in IEEE Transactions On Antennas and Propagation, vol. AP-23, January 1975. The disclosed embodiment of the present invention utilizes a directional antenna at a tracking/locating unit 200 (FIG. 2) to detect a direction of an individual, e.g., a child wearing a tracked unit 100 (FIG. 1).

In particular, FIG. 1 shows an embodiment of a tracked unit 100 worn by a tracked person in accordance with the principles of the present invention.

In FIG. 1, the tracked unit 100 includes an antenna 10, a transmitter and receiver circuit 11, a processor 12 such as a microcontroller, microprocessor or digital signal processor (DSP), memory 13, a code generator 14, and a battery 15. The tracked unit 100 may also include a panic button 16, a display 17, and/or a speaker 18.

Importantly, the tracked unit 100 further includes sensing means to sense a biological parameter of the person wearing the tracked unit 100. For instance, example biological sensors include a heart rate sensor 19 and a body temperature sensor 20. Heart rate may be sensed, e.g., using an infrared source and detector passing through a portion of the person's body, and body temperature may be sensed using infrared measurement for non-contact measurement, or any conventional thermistor or other temperature sensor for contact measurement.

An optional optical scanner 30, shown in phantom, can be used in conjunction with or instead of the heart rate sensor 19 and/or body temperature sensor 20 to detect unique physical characteristics of a region of the body directly adjacent to it. One example physical characteristic is a fingerprint measured by an optical scanner 30 worn on a finger of the tracked individual. Another physical characteristic scanned by the optical scanner 30 might be a small area of hair and skin on a wrist, or a pattern of a piece of clothing. This image would be digitized into a binary code and input to code generator 14. The actual image scanned is somewhat unimportant, only that the image scanned be capable of generating a substantially unique identifier for the specific wearer of the tracked unit 100.

Measurements taken by the sensing means is provided to a code generator 14 and forms the basis for the formation of a substantially unique ID code. The substantially unique ID code may be stored in memory 13 for repeated transmission, but is preferably repeatedly re-measured without necessarily storing the ID code in memory 13.

The transmitter and receiver circuit 11 transmits information to and may also receive information from a tracking/locating unit 200 (FIG. 2). When information is transmitted to the tracking/locating unit 200, the unique identifier ID code is sent along as part of the transmitted information. Using the substantially unique ID code, a parent or other tracking person can distinguish between multiple children or others wearing similar devices.

A processor 12 interfaces with and controls the operation of the tracked unit 100. A battery 15 supplies the necessary operating power for the circuitry and components. The battery 15 may be a standard carbon or lithium battery, or a rechargeable type battery such as nickel metal hydride (NiMH) or nickel cadmium (NiCAD).

The code generator 14 receives data from the biological parameter sensing means, e.g., from the heart rate sensor 19, body temperature sensor 20, and/or the optical scanner 30. The sensed biological data is combined by the code generator 14 to provide a substantially unique identifying code. For instance, the data may be directly transmitted as measured to the tracking/locating unit 200 (FIG. 2), or the data may be added, multiplied, or otherwise encoded to obtain a substantially unique code which is based at least in part on a biological parameter of the person wearing the device 100. The code generator 14 determines the unique code for each transmission is the tracking/locating unit 200, or on a frequent basis, to allow substantially immediate detection of changes in the status of the tracked person. For instance, repeated measurement of other biological parameters provides fast detection at the tracking/locating unit 200 of the unauthorized removal of a tracked unit 100.

The tracked unit 100 may further include a panic button 16 for communication with the tracking/locating unit 200, and/or a display 17 and/or a speaker 18 for conveying messages received from the tracking/locating unit 200.

Activation of the panic button 16 is sensed by the processor 12, and allows the wearer of the tracked unit 100 to contact and thus request immediate assistance from a monitoring person having a receiving tracking/locating unit 200. For instance, a child wearing the tracked unit 100 might be instructed to press the panic button 16 when they are lost, frightened, or find themselves in a dangerous situation, such as a possible kidnapping situation.

The display 17 of the tracked unit 100 can display simple alphanumeric messages from the tracking/locating unit 200. For example, a parent using the tracking/locating unit 200 might pass a message to a child wearing the tracked unit 100 such as "COME BACK NOW" or "MEET ME AT 7:00 PM".

The speaker 18 at the tracked unit 100 can be used similar to the display 17, i.e., to convey a message from the tracking/locating unit 200 to the wearer of the tracked unit 100. The audible message may be a voice transmission, a synthesized voice message, or one of a plurality of predetermined tones. Each predetermined tone can convey particular information with respect to locating and tracking, e.g., a high tone might indicate that the wearer is to stop moving, or is to return to a meeting point immediately. The predetermined tone may even simply draw the wearer's attention to the display 17.

Figure 3:
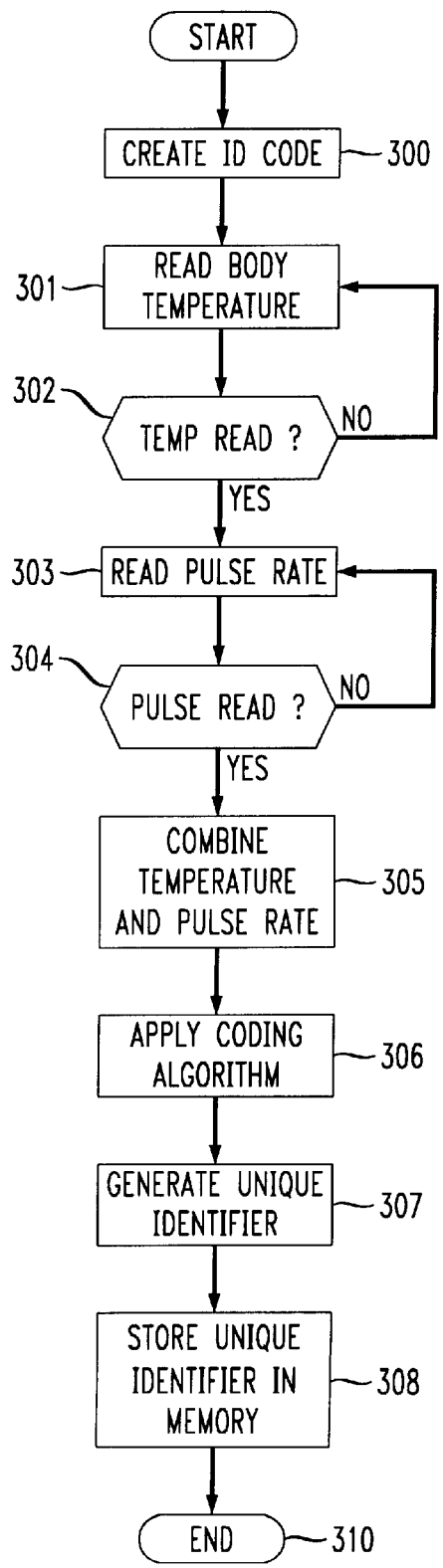
FIG. 3 is a flow chart illustrating the process steps in creating a unique identifier code in accordance with the principles of the present invention.
Figure 4:
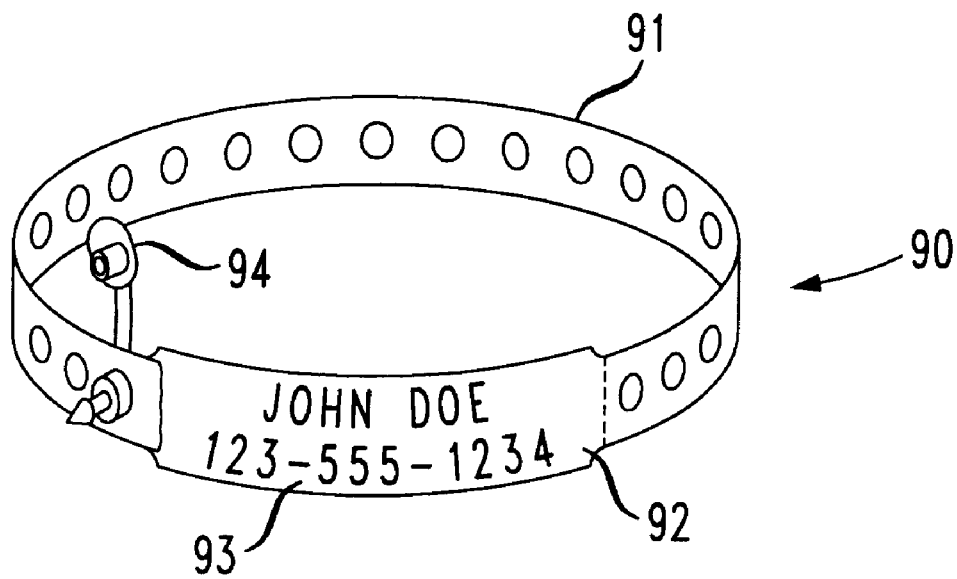
FIG. 4 is a conventional bracelet used to track and/or locate lost individuals.

FIG. 3 shows a flow chart of an embodiment of the code generator 14 shown in FIG. 1.

In FIG. 3, the code generation process is initiated in step 300. Step 301 obtains the wearing person's body temperature from the body temperature sensor 20, and repeats through step 302 if the temperature is not read or is not read properly (e.g., if it is outside of a normal expected range of body temperatures). If the body temperature is significantly out of range, it may indicate removal of the tracked unit 100, which may be interpreted as an alarm condition which is immediately reported to the processor 12 for transmission of an alarm message to the tracking/locating unit 200.

If the wearer's body temperature was read successfully, pulse or heart rate is measured in step 303, and repeated by step 304 until properly read. Similar to irregular temperature readings, an immediate alarm may be output to the processor 12 indicating an alarm condition if the heart rate is not within range, e.g., above 20 pulses per minute.

Step 305 combines the sensor data, e.g., body temperature, EKG, and/or heart rate in the disclosed embodiment, into a substantially unique ID code. A further coding algorithm may be applied in step 306 to the combined body temperature and/or heart rate, providing the substantially unique ID code in step 307. Lastly, the substantially unique ID code may be stored in memory 13 in step 308 and the process ends at step 310.

The ID code is referred to herein as "substantially" unique because of the remote possibility that more than one person may have the exact same body temperature and/or pulse rate. Moreover, it is recognized that even the same person's pulse rate and/or body temperature may change overtime. The unique ID code is relative, i.e., once the wearer puts on the worn device 100, the unique ID code will have some relatively unique value. Any subsequent absence of this substantially unique ID code in a transmission from a tracked unit 100 may indicate to the tracking/locating unit 200 that the wearer may have had the tracked unit 100 removed, and thus may be in danger. Transmissions from the tracked unit 100 allow the directional antenna 201 of the tracking/locating unit 200 to determine a direction of the tracked unit 100 with respect to the tracking/locating unit 200.

The substantially unique ID code generated by the code generator 14 need only be sufficiently unique to allow a tracking/locating unit 200 to distinguish between tracked units 100 within range of that particular tracking/locating unit 200.

After the substantially unique ID code is determined in the tracked unit 100, it is transmitted to the tracking/locating unit 200. FIG. 2 shows an embodiment of a tracking/locating unit 200 in accordance with the principles of the present invention.

In FIG. 2, the tracking/locating unit 200 includes a directional antenna 201 such as a YAGI directional antenna. The tracking/locating unit 200 further includes a transmitter and receiver circuit 202, a processor 203 (such as a microcontroller, microprocessor, or DSP), a battery 204, code memory 205, a pager key 206, and/or a display 207.

The transmitter and receiver circuit 202 of the tracking/locating unit 200 is tuned to receive a transmitted signal from corresponding tracked units 100, e.g., to a respective carrier frequency of the transmitter and receiver circuit 11 in the tracked units 100.

The tracking/locating unit 200 may further include a keyboard 208 forming input means. The keyboard 208 may be used, e.g., to input an identifying name in the processor 203 corresponding to the name, initials, or other identifying information with respect to persons wearing tracked units 100. This allows a parent or other tracking person to easily recognize and distinguish among particular children or other tracked persons.

The processor 203 interfaces with code memory 205 to store the incoming substantially unique identifying codes for the tracked units 100. The code memory 205 may include a plurality of substantially unique identifying codes corresponding to a plurality of tracked units 100, which may be organized in a table or database structure.

In operation, when a specific substantially unique ID code is received by the tracking/locating unit 200 via transmitter and receiver circuit 202, the corresponding label originally input to the processor 203 through the keyboard 208 (e.g., the child's name) is displayed on display 207. The display 207 may also indicate the specific heart rate, body temperature, and/or other biological parameters sensed by the tracked unit 100 if not encoded, to allow verification by the tracking/locating person that the wearer of the tracked unit 100 is still wearing the tracked unit 100, and that he or she is who they believe it to be. The tracking/locating unit 200 may decode or un-combine the biological parameter measurements from the received substantially unique ID code.

Alternatively, information in the processor 203 and/or memory 205 may be input via an external base station (not shown) to reduce the need for a large or full function keyboard 208 in the tracking/locating unit 200.

Activation of a pager key 206 detected by the processor 203 can be used to send a signal to the wearer of the tracked unit 100. If the tracking/locating unit 200 is in communication with more than one person wearing tracked units 100, then the display 207 can be utilized to obtain more information from the paging person before transmitting the paging signal. For instance, the display 207 can indicate questions to the tracking person with respect to which of the tracked persons in contact with the tracking/locating unit 200 is to be paged. Selection can be made via the keyboard 208, causing a paging signal to be transmitted by the tracking/locating unit 200 to the selected tracked unit 100. The paging signal may be received and indicated at the tracked unit 100, either on its display 17 and/or its speaker 18.

The biological parameters of the wearer can be measured when the tracked unit 100 is initially placed on the body of the wearing person. When removed, the biological parameters should preferably be reset in the memory 13 of the worn device 100 to prevent inaccurate transmissions falsely indicating that, e.g., a child is still wearing the tracked unit 100. Thus, if a kidnapper removes the tracked unit 100 from a kidnapped person for fear of being tracked, the removal of the tracked unit 100 will be immediately or soon thereafter be indicated to the tracking/locating unit 200. After reset, the tracked unit 100 may be worn by the same or a different individual as the code generation in the code generator 14 will be reactivated for transmission of a new substantially unique ID code based on biological parameters of the new wearer.

For tracking purposes, the tracking/locating unit 200 may detect a direction of the selected tracked unit 100 using its directional antenna 201. A tracking mode of the tracking/locating unit may be activated at all times, or upon selection by input through the keyboard 208.

In the tracking mode, the tracking/locating unit 200 may either wait for a periodic transmission from the desired tracked unit 100 or may instigate an immediate transmission by way of paging or other signal from the tracking/locating unit 200 to the tracked unit 100. In response, the tracked unit 100 will transmit a response signal to the tracking/locating unit 200, the direction of which can be detected by the YAGI directional antenna 201 in the tracking/locating unit 200, and which can be displayed on the display 207. The display 207 may display the substantially unique ID code or the name or initials of the tracked person.

The tracking mode is particularly advantageous in response to a panic button activation by the wearer of the tracked unit 100. In response, a person (e.g., a parent) may be alerted immediately to the needs of the wearer (e.g., a child).

One application of the present invention is in a retail environment. If a parent is going shopping with one or more children, tracked units in accordance with the present invention can be worn by the children, while a tracking/locating unit in accordance with the present invention can be used to track and/or locate the children as necessary. For instance, upon entering a store or mall, the parent could attach a tracking unit 100, shown in FIG. 1, to each of their children. The store may even rent these systems to the shoppers, to be used while they are in the retail establishment. The parent carries a corresponding tracking/locating unit 200, shown in FIG. 2, to monitor the whereabouts of their children.

A tracking unit 100 formed as a bracelet is but one example of a tracking unit 100 in accordance with the principles of the present invention. However, it is to be understood that the tracking unit 100 may take other forms. For instance, the tracking unit 100 may be formed into a pendant, belt, hat, glove, or other garment or device capable of being attached to an individual.

The present disclosure includes that contained in the appended claims, as well as that of the foregoing description. Other embodiments of the present invention, although not shown, are also contemplated. For example, a parent-child relationship was illustrated, but the system of the present invention could be used in any of many applications, such as a guardian and an elderly patient, a spouse and someone who may be suffering from Alzheimer's disease, etc. Moreover, a pet owner could track the location of a pet, such as a dog or cat.

Although this invention has been shown and described in illustrative embodiments, it is understood that the present invention is described by way of example and that numerous changes in the details of construction and/or the combination and arrangement of parts may be resorted to without departing from the spirit and scope of the invention.

What is claimed is:

1. A biotelemetry locating system used to track a desired individual, comprising:
   a mobile tracked unit comprising at least one biological sensor;
   a mobile tracking/locating unit;
   a code generator for generating a substantially unique identifying code based on data from said at least one biological sensor that measures a biological parameter that is substantially unique to a biological being;
   said mobile tracked unit being capable of transmitting said identifying code to said mobile tracking/locating unit.

2. The biotelemetry locating system according to claim 1, wherein said tracking/locating unit further comprises:
   a code memory for associating said identifying code generated by said code generator in said tracked unit with a wearer's name.

3. The biotelemetry locating system according to claim 1, wherein said at least one biological sensor senses at least one parameter selected from:
   a heart waveform as measured by an EKG; and
   a fingerprint.

4. The biotelemetry locating system according to claim 1, wherein said tracked unit further comprises:
   a panic button to activate an alarm signal transmitted to said tracking/locating unit.

5. The biotelemetry locating system according to claim 1, wherein said tracked unit further comprises:
   a display adapted to display a message received from said tracking/locating unit.

6. The biotelemetry locating system according to claim 1, wherein said tracked unit further comprises:
   a speaker to output an audible tone in response to a signal received from said tracking/locating unit.

7. The biotelemetry locating system according to claim 1, wherein said tracking/locating unit further comprises:
   a directional type antenna.

8. The biotelemetry locating system according to claim 1, wherein said tracked unit further comprises:
   an optical scanner to determine an optical biological parameter relating to a wearer of the tracked unit.

9. The biotelemetry locating system according to claim 7, wherein said tracking/locating unit further comprises:
   a display adapted to display a direction to said tracked unit.

10. The biotelemetry locating system according to claim 1, wherein said tracking/locating unit further comprises:
    a pager function adapted to activate a paging signal transmitted to said tracked unit.

11. A tracked unit of a biotelemetry locating system comprising:
    a biotelemetry sensor adapted to measure a biological parameter that is substantially unique to a wearer of said tracked unit;
    a code generator, coupled to said biological sensor, adapted to generate a substantially unique ID code based on said measured parameter; and
    a transmitter to transmit said substantially unique ID code.

12. The tracked unit according to claim 11, wherein:
    said biotelemetry sensor is an EKG sensor that measures a heart waveform.

13. The tracked unit according to claim 11, wherein:
    said biotelemetry sensor is a fingerprint scanner.

14. The tracked unit according to claim 11, further comprising:
    a transmitter; and
    a panic button to activate an alarm condition transmitted from said tracked unit.

15. A tracking/locating unit of a biotelemetry locating system comprising:
    a receiver circuit in a mobile unit;
    a processor, in communication with said receiver circuit, adapted to identify a substantially unique identifying code based on a biological parameter that is substantially unique to a wearer of a mobile tracked unit; and
    a display adapted to display a location of said mobile tracked unit based on a reception by said receiver of a signal including a substantially unique identifying code based on a biological parameter that is substantially unique to said wearer of said tracked unit.

16. The tracking/locating unit according to claim 15, further comprising:
    a directional antenna.

17. The tracking/locating unit according to claim 15, further comprising:
    a pager circuit adapted to transmit a paging signal to said tracked unit.

18. The tracking/locating unit according to claim 15, further comprising:
    a keyboard input device to said tracking/locating unit.

19. A biotelemetry locating system used to track desired individuals or animals, comprising:
    a tracking unit; and
    at least one tracked unit, said at least one tracked unit being adapted and arranged to generate a unique identification signal based on an algorithmic combination of a plurality of biological parameters of a wearer of said at least one tracked unit.

20. A method of tracking a biological being, comprising:
    measuring in a mobile tracked unit a biological parameter having a value that is substantially unique to said biological being;
    generating in said mobile tracked unit a substantially unique identifying code from said measured substantially unique biological parameter;
    transmitting in said mobile tracked unit said substantially unique identifying code to a mobile tracking unit.

* * * * *